United States Patent [19]

Klenk et al.

[11] 4,122,116
[45] Oct. 24, 1978

[54] SUBSTITUTED CYCLOPROPYL GLYOXYLNITRILES

[75] Inventors: Herbert Klenk; Heribert Offermanns, both of Hanau; Werner Schwarze, Frankfurt, all of Germany

[73] Assignee: Deutsche Gold- und Silber-Scheideanstalt vormals Roessler, Frankfurt, Germany

[21] Appl. No.: 880,483

[22] Filed: Feb. 23, 1978

Related U.S. Application Data

[63] Continuation-in-part of Ser. No. 802,944, Jun. 2, 1977.

[30] Foreign Application Priority Data

Feb. 25, 1977 [DE] Fed. Rep. of Germany ....... 2708183

[51] Int. Cl.² ..................... C07C 61/00; C07C 51/00; C07C 121/46
[52] U.S. Cl. ................................. 260/545 R; 71/113; 260/464
[58] Field of Search ............................... 260/545, 464

[56] References Cited

PUBLICATIONS

Hurd et al., J. Am. Chem. Soc., vol. 66, 2014 (1944).
Sperber et al., J. Am. Chem. Soc., vol. 72, 2793 (1950).
Normant et al., Bull. Soc. Chem. (France), pp. 2402–2403, (1972).
Rosenthal, Berichte Deutsch Chem. Gesell., vol. 44, 2465 (1911).

*Primary Examiner*—Gerald A. Schwartz
*Attorney, Agent, or Firm*—Cushman, Darby & Cushman

[57] ABSTRACT

There are prepared acyl cyanides of the formula

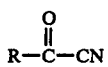 (I)

where R is a straight or branched chain alkyl group having 1 to 18 carbon atoms, preferably 1 to 10 carbon atoms, and which also can be substituted by one or more phenyl groups or halogen atoms, preferably chlorine, or R is preferably a cycloalkyl group having 3 to 8 carbon atoms, preferably cyclopropyl, which can have one or more 1 to 3 carbon atoms alkyl or halogen, preferably chlorine, substituents wherein in all of the above set forth substitutions the halogen atoms and the phenyl groups are not on the carbon atom adjacent to the carbonyl group or R is a substituted phenyl group, a naphthyl group, a substituted naphthyl group or a five membered heterocyclic group, e.g., furyl, thienyl or alkyl substituted thienyl wherein the substituents on the phenyl or naphthyl are halogen atoms, nitro groups or alkyl or alkoxy groups having 1 to 5 carbon atoms. The process comprises reacting and acyl halide of the formula R—CO—Hal   (II)

in which R is as defined above and Hal is a chlorine or bromine atoms, with CuCN at a temperature of about 50° to 180° C in the presence of a carboxylic acid nitrile inert under the reaction conditions, there being employed about 1 to 10 parts by weight of the carboxylic acid nitrile and about 0.5 to 20 parts by weight of at least one organic solvent which is inert under the reaction conditions. Certain of the compounds are novel per se.

6 Claims, No Drawings

SUBSTITUTED CYCLOPROPYL GLYOXYLNITRILES

This application is a continuation-in-part of Klenk et al. application Ser. No. 802,944 filed June 2, 1977. The entire disclosure of the parent application is hereby incorporated by reference and relied upon.

BACKGROUND OF THE INVENTION

The invention concerns a process for the production of acyl cyanides by reaction of carboxylic acid halides with metal cyanides at elevated temperature. Acyl cyanides are important intermediate products for example for the production of α-ketocarboxylic acids.

It is known that acyl cyanides can be produced by reacting a metal cyanide with a carboxylic acid halide. However, the previously known processes have considerable disadvantages.

Thus, in the production of aliphatic acyl cyanides there must be employed acid bromides since the reactability of the acid chloride is not sufficient. For example, acetyl chloride does not react with CuCN even at the boiling temperature and likewise no reaction is obtained with KCN at a temperature between 65° and 130° C. (C. D. Hurd, O. E. Edwards, J. R. Roach, J. Amer. Chem. Soc. 66 (1944), 2014). With pivaloyl chloride with CuCN to be sure it is possible to obtain a reaction but the reaction time of 20 hours is extremely long (N. Sperber, R. Fricano, J. Amer. Chem. Soc. 72 (1950), 2793).

It is also known to react certain aliphatic carboxylic acid nitriles with CuCN in boiling acetonitrile but the yields are very small. Thus, starting from acetyl chloride there is isolated only 50% of acetyl cyanide and from pivaloyl chloride only 16% pivaloyl cyanide (Normant, Bull. Soc. Chim. France, 1972, pages 2402-2403). Somewhat higher yields of benzoyl, p-nitrobenzoyl cyanide and p-methoxybenzoyl cyanide are shown as well as valeroyl cyanide.

Aroyl cyanides are somewhat more easily produced from aroyl chlorides and metal cyanides, but the reaction conditions are still very disagreeable. For example, in the production of p-methoxybenzoyl cyanide from p-methoxybenzoyl chloride there is used mercury cyanide and a temperature range of 125° to 130° C. (L. Rosenthal, Berichte deutsch Chem. Gesell. 44 (1911), 2465).

SUMMARY OF THE INVENTION

There has now been found a process for the production of acyl cyanides of the formula

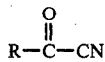
(I)

where R is a straight or branched chain alkyl group having 1 to 18 carbon atoms, preferably 1 to 10 carbon atoms, and which also can be substituted by at least one phenyl group or halogen atom, preferably chlorine, or R is preferably a cycloalkyl group having 3 to 8 carbon atoms, preferably cyclopropyl, which can have at least one alkyl substituent having 1 to 3 carbon atoms or halogen, preferably chlorine, with the proviso that in all of the above set forth substituents the halogen atoms and the phenyl groups are not on the carbon atom adjacent to the carbonyl group or R is a substituted phenyl group, a naphthyl group, a substituted naphthyl group or a five membered heterocyclic group, e.g., furyl, thienyl or alkyl substituted thienyl wherein the substituents on the phenyl or naphthyl are halogen atoms, nitro groups, alkyl groups having 1 to 5 carbon atoms or alkoxy groups having 1 to 5 carbon atoms. The process comprises reacting an acyl halide of the formula

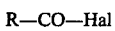
(II)

in which R is as defined above and Hal is a chloride or bromine atom with CuCN at a temperature of about 50° to 180° C. in the presence of a mixture consisting of about 1 to 10 equivalents of a carboxylic acid nitrile inert under the reaction conditions, and about 0.5 to 20 parts by weight of at least one organic solvent which is inert under the reaction conditions.

It is completely surprising that the reaction succeeds with both aromatic, e.g., aroyl, as well as aliphatic, e.g., acyl halides and with both acid bromides and acid chlorides and in all cases leads to very good yields.

Illustrative acyl halides of formula (II) which can be used in the reaction are acetyl chloride, pivaloyl chloride, propionyl chloride, isobutyryl chloride, isovaleroyl chloride, stearoyl chloride, decanoyl chloride, hexanoyl chloride, isodecanoyl chloride, furoyl chloride, 4-chlorobutyryl chloride, 3-chloropropionyl chloride, 5-chlorovaleroyl chloride, 3,3-dichloropropionyl chloride, 3-phenylpropionyl chloride, 4-phenylbutyryl chloride, 3-bromopropionyl chloride, 2-methylbutyryl chloride cyclopropane carboxylic acid chloride, cyclohexane carboxylic acid chloride, 1-methylcyclohexane carboxylic acid chloride, 1-methyl-2,2-dichlorocyclopropane carboxylic acid chloride, 1,3-dimethyl-2,2-dichlorocyclopropane carboxylic acid, 1,3-dimethylcyclopropane carboxylic acid chloride, cyclopentane carboxylic acid chloride, cyclooctane carboxylic acid chloride, 1-naphthoyl chloride, 2-naphthoyl chloride, 2-methylbenzoyl chloride, 3-methylbenzoyl chloride, 4-methylbenzoyl chloride, 2,4-dimethylbenzoyl chloride, 2-methyl-4-chlorobenzoyl chloride, 2,4-dichlorobenzoyl chloride, 4-chlorobenzoyl chloride, 2-chlorobenzoyl chloride, 4-fluorobenzoyl chloride, 4-nitrobenzoyl chloride, 3-nitrobenzoyl chloride, 4-ethylbenzoyl chloride, 4-isopropylbenzoyl chloride, 4-amylbenzoyl chloride, 4-t-amylbenzoyl chloride, 2-methoxybenzoyl chloride, 4-methoxybenzoyl chloride, 2,4-dimethoxybenzoyl chloride, 3-ethoxybenzoyl chloride, 3,4-dimethoxybenzoyl chloride, 4-amyloxybenzoyl chloride, 2-bromobenzoyl chloride, 1-propylcyclopropane carboxylic acid chloride, 2-chloronaphthoyl chloride, 3-nitronaphthoyl chloride, 2-methylnaphthoyl chloride, 2-mexhoxynaphthoyl chloride, acetyl bromide, pivaloyl bromide, 4-chlorobenzoyl bromide, cyclopropane carboxylic acid bromide. The acyl halides of formula II can be prepared by known method. E.g. 2,2-dichloro-1-methylcyclopropyl carbonic acid is reacted with the equivalent amount of thionylchloride at about 18° C. and the reaction product is distilled under reduced pressure.

Besides the simple procedure a substantial advantage of the process of the invention is that it is not limited to the production of special acyl cyanides, but it is virtually universally usable and it can be used to prepare previously unknown compounds, for example, (2,2-dichloro-1-methylcyclopropyl)-glyoxylnitrile and (2,2-dichloro-1,3-dimethylcyclopropyl)-glyoxylnitrile.

These latter compounds are useful to prepare the corresponding alpha keto carboxylic acids. They also are useful for insecticides.

There can also be prepared (1-methycyclopropyl)-glyoxylnitrile of the formula

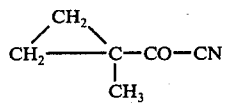

It can be used to prepare the corresponding alpha keto carboxylic acid. It also is useful as an intermediate in preparing herbicides which are superior to corresponding herbicides produced from simple (cyclopropyl) glyoxylnitrile. (Cyclopropyl) glyoxylnitrile is old pe se, Zhiral, Monatshefte fur Chemie Vol. 96 pages 1983 to 1999 (1965).

(1-methylcyclopropyl)-glyoxylnitrile can be prepared by the process set forth above in this "Summary of The Invention". However, it is preferably prepared by reacting 1-methyl-cyclopropane carboxylic acid chloride (or bromide) with a mixture of an alkali cyanide and a copper (I) salt in the presence of a carboxylic acid nitrile according to the procedure set forth in Klenk application Ser. No. 802,942 filed June 2, 1977. The entire disclosure of Klenk application Ser. No. 802,942 is hereby incorporated by reference and relied upon.

The reaction takes place in the presence of at least one carboxylic acid nitrile which is inert under the reaction conditions. Well suited are nitriles of simple monocarboxylic acids such as propionitrile or benzonitrile. There can also be used for example butyronitrile, isobutyronitrile, valeronitrile, capronitrile, caprylonitrile, lauronitrile, o-toluonitrile, p-toluonitrile or m-toluonitrile. Preferred nitrile is acetonitrile. Although very large amounts of nitrile can be used it is advantageous to add only a slight overstoichiometric amount of carboxylic acid nitrile. Preferably there is used about 1.05 to 5.0 equivalents (moles) of carboxylic acid nitrile per mole of acid halide. Less preferably there can be used less nitrile, e.g., about 0.1 to 1.0 mole of nitrile per mole of acid halide.

The reaction takes place in the presence of CuCN. It is generally suitable to use overstoichiometric amounts of CuCN. It is advantageous to use 1.05 to 2 equivalents (moles) of CuCN per mole of acid halide.

As inert organic solvents there can be used, for example, hydrocarbons, e.g., aromatic hydrocarbons such as benzene, toluene or xylene as well as mesitylene, ethyl benzene, cumene, p-cymene, t-butyl benzene or 1,3,5-triethyl benzene or aliphatic hydrocarbons such as ligroin with a boiling range of about 90° to 140° C., pentane, hexane, heptane, octane or decane or cyclic hydrocarbons, such as decalin, cyclohexane and tetralin or halogenated hydrocarbons, particularly chlorinated aromatic or aliphatic hydrocarbons, such as chlorobenzene, dichlorobenzene, symmetrical tetrachloroethane, chloroform, dichloroethylene, carbon tetrachloride, trichloroethylene, methylene chloride, trimethylene bromide, dibromoethylene, ethylene dibromide. Also as the solvent there can be used for example ethers, e.g., dioxane, dibutyl ether, dioxolane, ethylene glycol diethyl ether, ethylene glycol dibutyl ether, ethylene glycol dimethyl ether or esters, e.g., alkyl esters, e.g., alkyl alkanoates, such as butyl acetate, propyl acetate, amyl acetate, isobutyl acetate, octyl acetate, ethyl propionate, methyl butyrate, ethyl butyrate or methyl valerate. Mixtures of such solvents can be used.

In selecting the inert organic solvent to use both as to type and amount the thought is to make it easy to separate it from the acyl cyanide formed.

The reaction temperature can be varied within wide limits and depends on the type of solvent and the reactants. Generally, there is used a temperature of about 50° to about 180° C., particularly from 70° to 130° C. Although the pressure can be selected substantially at random it is advantageous not to deviate substantially from normal pressure, i.e., atmospheric pressure.

Unless otherwise indicated, all parts and percentages are by weight.

The materials employed can comprise, consist essentially of or consist of those set forth.

DESCRIPTION OF THE PREFERRED EMBODIMENTS

EXAMPLE 1

There were mixed in a reaction vessel provided with a reflux condenser 154.5 grams (1.0 mole) of 4-methylbenzoyl chloride with 117 grams (1.3 moles) of copper (I) cyanide, 150 ml of toluene and 61.5 grams (1.5 moles) of acetonitrile. The mixture was heated to 110° C. with stirring, held for 3 hours at this temperature and then cooled to 20° C. The salt separated thereby was filtered off and washed twice, each time with 50 ml of toluene. The filtrate was fractionally distilled at reduced pressure. There were recovered 137 grams of pure 4-methylbenzoyl cyanide, corresponding to a yield of 95% based on the acid chloride employed. The 4-methylbenzoyl cyanide had a boiling point of 100° to 103° C. at 20 mbar.

EXAMPLE 2

The procedure was the same as that described in Example 1 but instead of toluene there were used 250 ml of dichloroethane and the mixture was heated only to 90° C. There were isolated 125 grams of 4-methylbenzoyl cyanide, corresponding to a yield of 87% based on the acid chloride employed. The 4-methylbenzoyl cyanide had a boiling point of 107° to 110° C. at 28 mbar.

EXAMPLE 3

Using the method described in Example 1, there were produced the compounds entered in the following table:

| | R—CO—CN | | |
|---|---|---|---|
| Compound No. | R | Yield (%) | Boiling Point C / mbar |
| 1 | ⌬-CH₃ | 90 | 108 – 110 / 20 |
| 2 | Cl-⌬ | 87 | 114 – 116 / 17 |
| 3 | ⌬-Cl | 87 | 120 – 123 / 17 |

-continued

| Compound No. | R | Yield (%) | Boiling Point C / mbar |
|---|---|---|---|
| 4 | 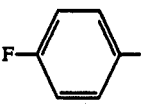 | 85 | 85 – 88 / 20 |
| 5 | 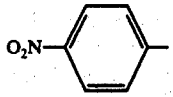 | 75 | 162 – 163 / 17 |
| 6 | 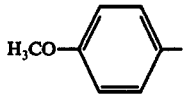 | 91 | 157 – 158 / 16 |
| 7 | 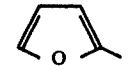 | 83 | 74 – 77 / 15 |
| 8 | 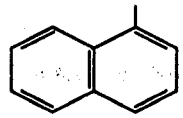 | 90 | 179 – 182 / 20 |
| 9 | 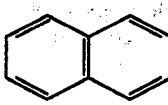 | 90 | 150 / 7 |
| 10 | 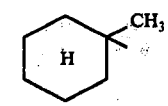 | 92 | 79 – 81 / 17 |
| 11 | 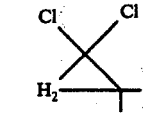 | 84 | 81 – 82 / 14 |
| 12 | 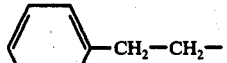 | 80 | 117 – 119 / 15 |
| 13 | Cl—CH$_2$—CH$_2$—CH$_2$— | 76 | 88 / 25 |
| 14 | 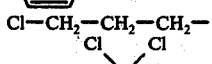 | 70 | 85 – 86 / 10 |

R—CO—CN

EXAMPLE 4

There were mixed in a reaction vessel provided with a reflux condenser 157.0 grams (2.0 moles) of acetyl chloride with 270 grams (3 moles) of copper (I) cyanide, 400 ml of 1,2,3,4-tetrahydronaphthalene and 164 grams (4 moles) of acetonitrile. The mixture was heated to boiling with stirring and held for 4 hours at reflux. Then it was cooled, the salt filtered off and washed twice, each time with 50 ml of tetrahydronaphthalene. The filtrate was fractionally distilled. The first fraction having a head temperature of 110° C. was removed. The weight of this fraction was 291 grams and contained according to gas chromatogram of 39.5% acetyl cyanide. This means a yield of 84% of acetyl cyanide based on the acetyl chloride employed.

EXAMPLE 5

The procedure was the same as in Example 4 except that instead of acetyl chloride there were used 241 grams (2.0 moles) of pivaloyl chloride. The fractional distillation resulted in 201 grams of pure pivaloyl cyanide, corresponding to a yield of 92% based on the pivaloyl chloride employed. The pivaloyl cyanide had a boiling point of 117° to 122° C. at normal pressure.

EXAMPLE 6

The following compounds were produced by the process described in Example 5:

| Compound No. | R | Yield (%) | Boiling Point C / mbar |
|---|---|---|---|
| 1 | CH$_3$—CH$_2$— | 75 | 106 – 110 / 1015 |
| 2 | 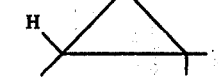 | 80 | 61 – 62 / 133 |
| 3 |  | 80 | 71 – 74 / 120 |
| 4 | 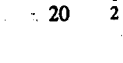 | 81 | 68 – 70 / 135 |
| 5 |  | 85 | 92 – 93 / 160 |

R—CO—CN

EXAMPLE 7

(1-methylcyclopropyl)-glyoxylnitrile (also called 1-methylcyclopropylcarbonylcyanide)

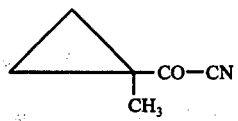

There were placed in a 3-tubed round bottom flask a mixture of 14% grams of finely divided sodium cyanide and 27 grams of copper (I) cyanide in a mixture of 81 grams of acetonitrile and 300 ml of tetralin. This mixture was heated with stirring to 88°–90° C.

At this temperature there were run in within one hour 237 grams of 1-methylcyclopropyl carboxylic acid chloride, subsequently it was boiled under reflux for 2 more hours. Therewith the internal temperature increased to 110° C. Then the mixture was cooled, the salt filtered off with suction and washed with tetralin. The filtrate was then rectified in a vacuum on a 1-meter Vigreux column (with dephlegmator). At B.P.$_{10}$ 44°–45° C. 1-methyl-cyclopropyl-glyoxylnitrile distilled.

Amount 181.8 grams = 83.4% of theory. It was a water clear liquid.

Elemental analysis: C$_6$H$_7$NO (Mol. weight 109) — Calculated: C 66, H 6.4, N 12.8; Found: C 65.8, H 6.4, N 12.7.

1-methyl-cyclopropyl-glyoxylnitrile is useful as an intermediate in making the herbicide 4-amino-6-(1-methylcyclopropyl)-3-methylthio-1,2,4-triazin-5-one as is set forth in German patent application No. 2,732,797 filed in Germany on July 20, 1977. The following disclosure is taken from that application.

EXAMPLE 8

(a) Production of (1-methyl-cyclopropyl)-glyoxyl-tert. butylamide

109 Grams of (1-methyl-cyclopropyl)-glyoxylnitrile (1 mole) were added to a mixture of 130 grams of t-butanol and 130 ml of methylene chloride. Then there were dropped in with stirring at 0° to 5° C. 100 grams of 98% sulfuric acid, the temperature increased to 20° C. and the mixture was stirred for 4 hours. Then there were added 18 ml of water and stirring continued again for 30 minutes. The mixture was diluted with 500 ml of methylene chloride and the pH adjusted to 6 with aqueous NaOH with cooling. The methylene chloride solution was then evaporated. There remained 181 grams (= 98.9%) of (1-methyl-cyclopropyl)-glyoxyl-tert. butylamide, M.P. 80° C.

Analysis: Calculated: C 65.5, H 9.3, N 7.65; Found: C 65.2, H 9.4, N 7.45.

(b) Production of 4-amino-6-(1-methyl-cyclopropyl)-3-mercapto-1,2,4-triazin-5-one 183 Grams of (1-methyl-cyclopropyl)-glyoxyl-tert. butylamide and 112 grams of thiocarbohydrazide were placed in a mixture of 1 liter of 1 N HCl and 1 liter of ethanol. The mixture was boiled under reflux for 8 hours, cooled, diluted with 2 liters of water and the crystals filtered off with suction. There were obtained white crystals with a yellow luster, which were dried.

Amount: 152.6 grams = 77.1% of theory;
M.P. 137° to 138° C.
Analysis: Calculated: C 42.4, H 5.05, N 28.3, S 16.16; Found: C 42.2, H 5.1, N 28.1, S 16.1.

$C_7H_{10}N_4O_2$
(Mol. wt. = 198)

(c) Methylation To 4-amino-6-(1-methyl-cyclopropyl)-3-methylthio-1,2,4-triazin-5-one 198 grams of the compound obtained in (b) were dissolved in 500 ml of 2N $N_aOH$ and there were added 500 ml methanol and 150 grams of methyl iodide. The mixture was stirred for 6 hours at 20° to 30° C. The crystals formed were filtered off with suction, washed and dried. There were obtained 174.5 grams of the final product (dried in a vacuum at 40° C.), white crystals, M.P. 115° to 116° C.

Yield 82.3% of theory.
Analysis: Calculated: C 45.3, H 5.7, N 26.4, S 15.1; (Mol. wt. = 212); Found: C 45.3, H 5.8, N 26.1, S 15.3.

EXAMPLE 9

The herbicidal activity of the 1,2,4-triazin-5-one derivative was ascertained by the following experiments:

The herbicidal activity was determined by application of the active material as a pre-emergent herbicide.

Test plants were sown in frames in the greenhouse, specifically cultivated plants and mono and dicotylledon weeds. After sowing the active material of Example 8 having the formula

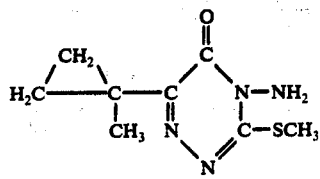

as well as a commercial triazone derivative were sprayed on as aqueous-ethanolic dispersions. The evaluation of the effect produced on the rising plants were made 28 days after the application. During the tests the plants were maintained equally moist.

The evaluation took place according to the following scale of 1 to 6.
1. Plants undamaged
2. Moderate growth
3. Plants below normal
4. Slight damage
5. Severe damage
6. Total kill Compounds Tested:
A: 4-amino-6-t-butyl-3-methylthio-1,2,4-triazin-5-one (known)
B: 4-amino-6-(1-methyl-cyclopropyl)-3-methylthio-1,2,4-triazin-5-one (compound made in Example 8)

| Test Plants | 250 grams/hectare | | 500 grams/hectare | |
|---|---|---|---|---|
| | A | B | A | B |
| Stellaria media | 6 | 6 | 6 | 6 |
| Sonchus asper | 6 | 6 | 6 | 6 |
| Polygenum lanceolota | 6 | 6 | 6 | 6 |
| Matricaria indodora | 6 | 6 | 6 | 6 |
| Galium aparine | 1 | 6 | 5 | 6 |
| Echinochloa crus-galli | 6 | 6 | 6 | 6 |
| Digitaria album | 6 | 6 | 6 | 6 |
| Digitaria sanguinalis | 6 | 6 | 6 | 6 |
| Centaurea cyanus | 6 | 6 | 6 | 6 |
| Avena fatua | 6 | 6 | 6 | 6 |
| Amaranthus retroflexus | 6 | 6 | 6 | 6 |
| Agropyron repens | 6 | 6 | 6 | 6 |
| Sinapis alba | 6 | 6 | 6 | 6 |
| Brassica napus | 6 | 6 | 6 | 6 |
| Beta vulgaris | 6 | 6 | 6 | 6 |
| Pharaeolus vulgaris | 6 | 6 | 6 | 6 |
| Zea mais | 2 | 5 | 4 | 6 |
| Soja hispida | 5 | 6 | 6 | 6 |
| TFriticum aestivum | 6 | 6 | 6 | 6 |
| Secale cereale | 6 | 6 | 6 | 6 |
| Poa annua | 6 | 6 | 6 | 6 |
| Lolium perenne | 6 | 6 | 6 | 6 |
| Hordeum vulgare | 5 | 6 | 6 | 6 |
| Avena sativa | 6 | 6 | 6 | 6 |
| Apera spica venti | 6 | 6 | 6 | 6 |
| Alopycurus myosuroides | 6 | 6 | 6 | 6 |
| Agrostis tenuis | 5 | 6 | 6 | 6 |

What is claimed is:
1. A compound having the formula

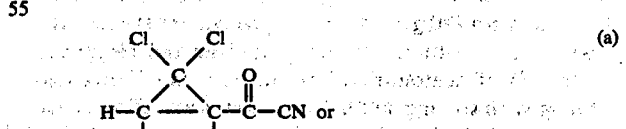

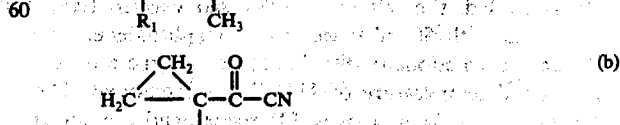

where $R_1$ is hydrogen or methyl and $R_2$ is alkyl of 1 to 3 carbon atoms.

2. A compound according to claim 1 having formula (a).

3. A compound according to claim 2 wherein $R_1$ is hydrogen.

4. A compound according to claim 2 wherein $R_1$ is methyl.

5. A compound according to claim 1 having formula (b).

6. A compound according to claim 5 wherein $R_2$ is methyl.

* * * * *